United States Patent [19]

Lindsay et al.

[11] Patent Number: 5,106,729
[45] Date of Patent: Apr. 21, 1992

[54] METHOD FOR VISUALIZING THE BASE SEQUENCE OF NUCLEIC ACID POLYMERS

[75] Inventors: Stuart M. Lindsay, Tempe, Ariz.; Manfred Philipp, Scarsdale, N.Y.

[73] Assignee: Arizona Board of Regents acting on behalf of Arizona State University, Tempe, Ariz.

[21] Appl. No.: 384,412

[22] Filed: Jul. 24, 1989

[51] Int. Cl.$^5$ ............................................... C12Q 1/68
[52] U.S. Cl. .................................... 435/6; 435/91; 435/810; 250/306; 250/307; 250/311; 436/501; 536/27; 935/77; 935/86; 935/87; 935/88
[58] Field of Search ............... 435/6, 810, 91; 536/27; 436/501; 935/77, 88, 86, 87; 250/306, 307, 311

[56] References Cited

U.S. PATENT DOCUMENTS 4,711,955  12/1987  Ward et al. ........................... 536/27

OTHER PUBLICATIONS

Lindsay et al. (1989) Science, vol. 244, pp. 1063-1064.

Primary Examiner—Amelia Burgess Yarbrough
Assistant Examiner—Ardin H. Marschel
Attorney, Agent, or Firm—Richard R. Mybeck

[57] ABSTRACT

A method for determining and visualizing the base sequence of nucleic acid polymers, especially DNA and RNA, with a scanning probe microscope having a tip, the method including replacing the oxygen in the nucleic acid polymer with sulfur, complexing the sulfur with a metal such as mercury, and passing the tip over the complexed polymer in a scanning path to measure the potential and record the difference in electrical conductivity at preselected increments along the scanning path.

20 Claims, 1 Drawing Sheet

[5,106,729]

METHOD FOR VISUALIZING THE BASE SEQUENCE OF NUCLEIC ACID POLYMERS

TECHNICAL FIELD

The present invention relates to means and methods for visualizing the base sequence of nucleic acid polymers and more particularly to determining and visualizing the nucleotide sequence of deoxyribonucleic acid (DNA) and ribonucleic acid (RNA).

BACKGROUND OF THE INVENTION

The ability to sequence DNA rapidly is a major goal of modern medicine. One well-publicized effort includes the project to sequence the human genome. However, since each human chromosome contains some $10^9$ base pairs, current technology based on wet-chemistry sequencing methods (See: F. Sanger. "Determination of Nucleotide Sequences in DNA. *Science* 214. 1205-1210, 1980; and W. Gilbert, "DNA Sequencing and Gene Structure", *Science,* 214, 1305-1312, 1981) is just not useful for a project of that magnitude. Indeed, to date, there is no known method of simply determining and visualizing the sequence of a given fragment in a microscope. The present invention provides such a method for imaging and sequencing DNA/RNA molecules with a scanning tunneling microscope (STM) or an atomic force microscope (AFM) while avoiding the distortions caused by prior methodologies.

BRIEF SUMMARY OF THE DISCLOSURE

The present invention relates to a method for visualizing the base sequence of nucleic acid polymers and more particularly to methods of imaging nucleic acids using a scanning tunneling microscope (STM) or an atomic force microscope (AFM). As will hereinafter appear in greater detail, the present invention allows fully hydrated DNA and RNA to be imaged undistorted by the metallic stains used in electron microscopy so that it is viewed in the exact configuration it maintains within living organisms. One major limitation of STM and its first cousin, the atomic force microscope ("AFM"), is the limited resolution caused by the distortion of soft biological molecules as they interact with the tip of the STM or AFM (hereinafter collectively referred to as "STM"). In the best cases, such resolution approaches half a nanometer, far too poor to identify the chemical composition of the nucleic acids at the level of the base sequence.

The present disclosure is based on the remarkably unexpected discovery that the presence of a compound of a metal, such as mercury, in a neutral or in an ionized state, when complexed with the nucleic acid, leads to enhanced contrast in the STM thereby enabling the base sequence of nucleic acid polymers to be quickly and unequivocally elucidated. Thus, it is possible to measure the response of the scanning probe microscope having an electrically conductive tip operatively associated therewith to a change in conductivity resulting from its encounter with a complexed metal atom such as mercury. The conductivity can be measured directly or indirectly by observing a change in electrical potential between the tip and the substrate.

Accordingly, it is a prime object of the present invention to provide a novel and unique method for determining and imaging the sequence of nucleic acids under water using a scanning tunneling microscope (STM).

Another object of the present invention is to provide a novel and unique method to image DNA and RNA undistorted by the metal stains used in electron microscopy and while fully hydrated so that its viewed configuration exactly conforms to the configuration it maintains within living organisms.

A further object of the present invention is to provide a novel and unique method for imaging DNA and RNA in which the presence of a preselected metal atom, bonded to the nucleic acid, provides enhanced contrast in the STM.

These and still further objects as shall hereinafter appear are readily fulfilled by the present invention in a remarkably unexpected manner as will be readily discerned from the following detailed description of an exemplary embodiment thereof especially when read in conjunction with the accompanying drawing in which like parts bear like numerals throughout the several views.

DESCRIPTION OF THE PREFERRED EMBODIMENTS

Figure 1:
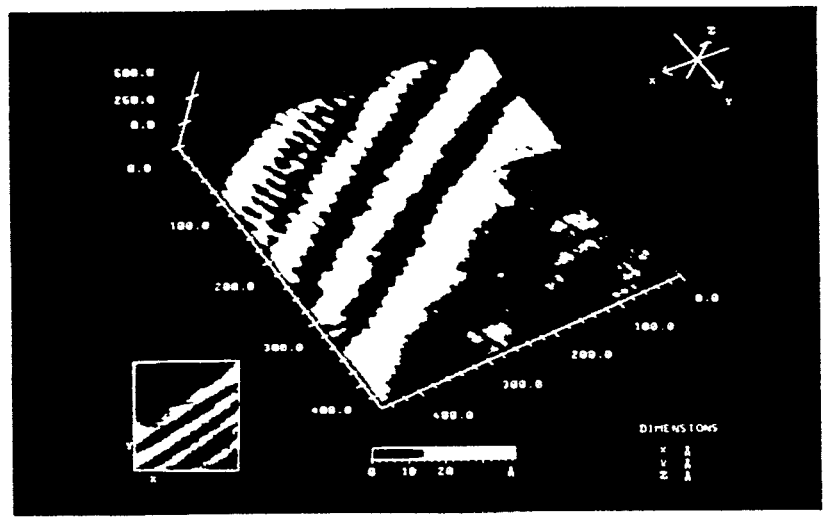
FIG. 1 is a perspective image of two polyuridylic acid (poly (rU)) molecules on a 420 Å × 420 Å substrate showing resolution of features as small as 6 Å, the top view being shown in inset.

The present invention relates to a method for determining and imaging nucleic acids under water using a scanning tunneling microscope ("STM") based on the presence of a metal atom, such as mercury, bonded to the nucleic acid. The method provides remarkably and unexpectedly enhanced contrast.

Thymidine, uridine, guanosine and cytidine nucleosides all contain oxygen in their thymine, uracil, guanine, and cytosine bases. Each has known derivatives in which one of its oxygen molecules is replaced by divalent sulfur. Examples are $S^2$-thymidine, $S^4$-thymidine, $S^2$- uridine, $S^4$-uridine, $S^6$-guanosine, and $S^2$- cytidine The nucleoside bases can potentially also contain divalent sulfur, useful herein at other positions such as on the 5-methyl group of thymidine.

The ribose portion of nucleosides also contain oxygen which can be replaced by divalent sulfur, such as in the 2'-deoxy-2'-thionucleosides, an example of which is 2'-deoxy-2'-thiocytidine. Nucleotides containing such divalent sulfur are also useful in the practice of the present invention.

Such base-modified and/or sugar-modified nucleosides can be prepared as the analogous ribonucleotide 5'-triphosphates and used in the synthesis of RNA. Such base-modified 2'-deoxynucleosides can also be prepared as the analogous 2'-deoxyribonucleotide-5'-triphosphates and used in the synthesis of DNA.

Also, modified nucleosides 5'-triphosphates have been prepared in which the alpha-phosphate group contains a divalent sulfur. Such 2'-deoxy compounds have the general formula

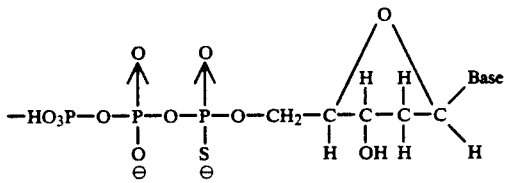

Such ribonucleotides have the general formula

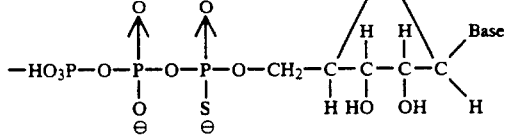

where, in both cases, the alpha-S isomer is the preferred substrate for nucleotide polymerizing enzymes.

The word "Base" indicates the position of the five common nucleoside bases and their derivatives, namely cytosine, uracil, thymine, guanosine, or adenine. Nucleotides containing modified purine bases can also be used, such as inosine and 7-deazaguanosine nucleotides. Nucleotides containing modified pyrimidine bases can also be used, such as the 5-substituted pyrimidine nucleotides containing 5-bromo-, 5-fluoro-, or 5-iodouracil. Any base-substituted phosphate-substituted, or sugar-substituted nucleotide used, which maintains base-pairing specificity, and is compatible with the presence of the essential sulfur atom needed for this invention can be used in this invention.

Polymerization of the alpha-thio-2'-deoxynucleoside 5'-triphoshates (or 2'-deoxynucleoside 5'-O-(1-thiotriphosphates) with DNA polymerizing enzymes yields polymers of the general structure shown below.

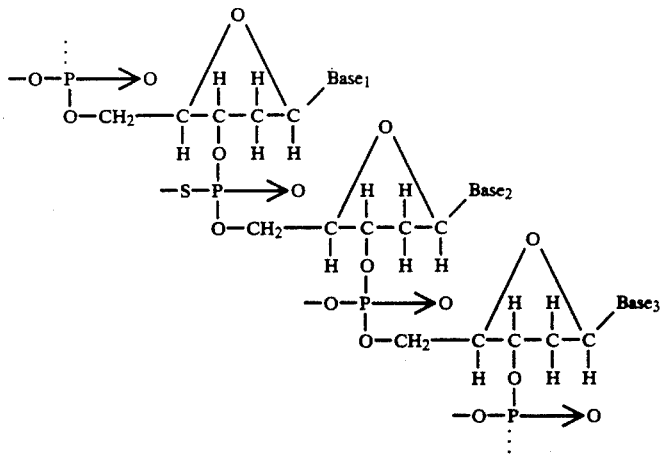

Polymerization of the alpha-thio-ribonucleotide 5'-triphosphates with RNA polymerizing enzymes yields polymers of the general structure shown below.

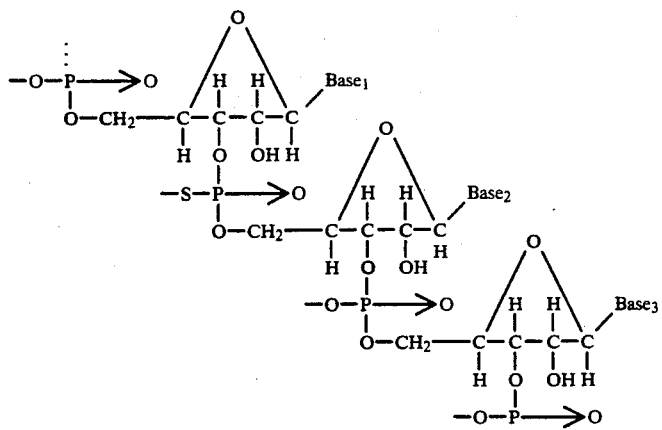

In the two polymers shown above, base-2 results from incorporation of an alpha-thionucleoside-5'-triphosphate, while the other bases result from incorporation of non-sulfur-containing nucleoside 5'-triphosphates.

The divalent sulfur in these polynucleotides complexes with the metal atoms present in the compounds added for the purpose of specific nucleotide labeling. This results in selective staining of those sites in the polynucleotides that contain divalent sulfur.

The mercury compounds or other metal-containing compounds added to the solution for the purpose of labeling the DNA or RNA are present as cations and/or are bonded to other chemical groups.

Without wishing to be bound by any theory of operation, it is believed that mercury forms an amalgam with gold, a material preferred herein as a standard substrate. Thus, the present invention provides a method in which a metallic cluster may be formed between selected sites on the nucleic acid and the gold substrate. Subsequent imaging in water allows greater control of the deposition and the nature of the interface and is therefore preferred although favorable results can be obtained with a sample dried in air.

In accordance with the present invention, a nucleic acid is sequenced by selecting a fragment for sequencing. While such a selection is a prerequisite for any sequencing technique, in STM it is straightforward to hold down and image at least 146 base-pair fragments (See: S. M. Lindsay et al,. *Science* Vol. 244, pp. 1063–64 (1989)).

For convenience, certain generally accepted abbreviations are used herein having the following meanings: Poly (U) and Poly (rU) are interchangeable and identify "polyuridylic acid"; poly (dT) identifies "polythymidylic acid"; and poly (s⁴U) identifies "poly-4-thiouridylic acid".

In one practice of the present invention, the original fragment is amplified using the general procedure described in U.S. Pat. No. 4,683,202 but employing a sulfur-substituted variant for the monophosphate derivative of one of the bases. The resulting polymer is dissolved in a buffer that consists in part of a metal-containing inorganic compound or an organometallic compound such as sodium-4-hydroxymercuribenzoate ("PCMB"), which binds the sulfur-containing sites, and yields enhanced contrast at mercury bound sites as described below. The relative location of all the marked sites along the chain is recorded.

The material is then synthesized with another divalent sulfur-labeled nucleotide, and the imaging is repeated. In principle, the sequence will be determined when three of the four normal nucleotides are replaced with a divalent sulfur-containing nucleotide. However, it will help to resolve ambiguities caused by lack of resolution of near neighbors to image the fourth base. Another possibility is to image the various combinations of pairs of bases in order to resolve ambiguities caused by inadequate resolution.

RNA is a stiffer polymer than DNA, and the images obtained for poly (U) show features down to ~5 Å, a much better resolution than our best DNA pictures. It is possibly advantageous, therefore, to transcribe the RNA analog of the fragment to be sequenced.

Especially unique to the present invention and, in large part, salient to the unexpected results obtained thereby is a new procedure for making substrates that are atomically flat (to within a few single atom steps). These substrates are flat over an overall surface area of one square micron. The present invention also provides a unique method for improving microscope tip insulation, by etching tips with a hard wax which insulates them and yet enables them to detect sample surface variations A preferred wax for this has a softening point of 80°–90° C., a vapor pressure of $10^{-3}$ mm at 180° C., and is available as Apiezon wax from VWR Scientific (San Francisco, Calif.). Any wax that has these properties may be used in this invention. These procedures will now be described in detail.

The substrates are made by depositing between a few hundred and a few thousand Å of gold epitaxially on freshly cleaved scratch-free mica in an ultra high vacuum ("UHV") system. The substrate is preheated to 300° C. in an oil-free system operated at $10^{-9}$ torr or better. The coated substrates are removed and stored under clean argon until use.

The tips are etched from 0.01 inch diameter Pt-Ir wire (e.g., Englehard material #26) using 3M NaCN containing 1M NaOH. The wire is immersed into the solution with 20V ac applied until 0.5A rms flows. It is then left until the waist at the liquid-air interface is just about to break. The current is stopped, and small bursts of current are applied to the junction as it is monitored under a microscope. When the lower region just parts, the etch is stopped. The overall shape of the end is quite rounded with a very small and sharp 'nipple' on the very end. The tip is insulated by being pushed through a film of Apiezon wax. This wax was found to be electrochemically inert in an aqueous environment. The temperature of the wax must be carefully controlled. If it is too hot, it flows off the tip as it penetrates, leaving too much metal exposed. If it is too cold, the end of the tip does not penetrate the wax.

In the preferred practice, the wax is melted onto a slot in a thin metal plate, adjusting the heating of the plate so that the hottest part of the slot is about 200° C., and the open end somewhat below the melting temperature of the wax. A blob of wax is melted onto the slot so as to form a film over it. The tip is then pushed through the wax film until it can be seen to just push a bit of wax ahead of it as it breaks the top of the film. The tip is then translated into a slightly hotter region. SEM imaging shows that a micron (or less) of bare metal penetrates the wax. Once pushed up enough to be usefully coated, the tip is translated sideways out of the slot.

The nucleic acid polymer whose sequence is to be determined is then prepared in the following manner. A sample of the unknown polymer is dissolved to a concentration of about 10 micrograms per ml in a buffer containing 10 mM tris and the appropriate mercury solution. Small amounts of EDTA, cacodylic acid and other preservatives may be used with no loss of resolution. A glass cell is pushed onto the substrate (it can be held with vacuum grease if its polish is inadequate for an interference fit). A few tens of microliters of sample solution are placed in the cell. About 1 mm of Pt-Ir wire is pushed into the sample, and biased to cause hydrogen evolution (the substrate being held positive). This requires about 2 V. The Faradaic deposition is continued for about two minutes. The STM tip is then lowered onto the substrate, and images are made in the usual way. With these conditions, the surface should not be uniformly coated, and isolated strands of polymer should be found in many regions.

STM IMAGES OF STAINED POLYMERS

Using a conventional STM and a computer controlled receiver and display system (Angstrom Technology, Inc., Mesa, Ariz.), the mercury stained fragments show increased contrast with images of poly (rU) which has had the oxygen on the C4 atom replaced with sulfur (poly s$^4$U). The mercury (II), needed to complex the sulfur, is provided by using a tris buffer containing about $2 \times 10^{-3}$M sodium 4-hydroxymercuribenzoate. While the exact concentrations do not appear to be critical, the conditions actually used to obtain the various images are described below.

Solution I contained 43 micrograms per ml of poly (rU) in 10 mM Tris, 1 mm EDTA, 1 mM NaN$_3$ adjusted to pH8 with cacodylic acid our standard buffer hereinafter identified as "SB".

Solution II consisted of a similar mix of poly (s$^4$U) in SB. After preparation, about 50 microliters of 2.4 mM sodium p-hydroxymercuribenzoate (in 10 mM tris, pH8) was added to 1 ml of the poly s$^4$U solution.

Solution III consisted of a 50-50 mix of Solutions I and II.

Solution IV consisted of 23 micrograms per ml of a selected sequence fragment of RNA, a total of 1,300 bases long.

The RNA is a transcript made in the presence of alpha-thio ATP. After its synthesis, it was labelled with mercury in the form of sodium 4-hydroxymercuribenzoate.

Referring to the drawing, the polymer used to create FIG. 1 had not been imaged before and a high resolution image of the pure poly (rU) is shown in FIG. 1. In FIG. 1, a 420 Å by 420 Å area of the substrate traversed by two molecules is shown. Although the relative contrast of the two molecules is somewhat different, depending on how each is embedded by surrounding reacted small anions, each shows the characteristic negative contrast as the molecule is approached (the tip appears to dip down relative to the substrate), followed by positive contrast, due, in part, to the constant current servo response. Internal structure is clearly resolved. The polymer appears to be a zig-zag with alternating 6 Å and 8 Å runs. This image is a perspective projection looking into the xy plane at an angle of about 45° with respect to all three axes.

Figure 2:
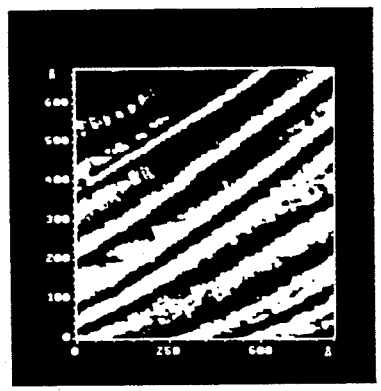
FIG. 2 is a head-on view of a 700 Å × 700 Å region showing at least six polyuridylic acid molecules crossing the substrate.
Figure 3:
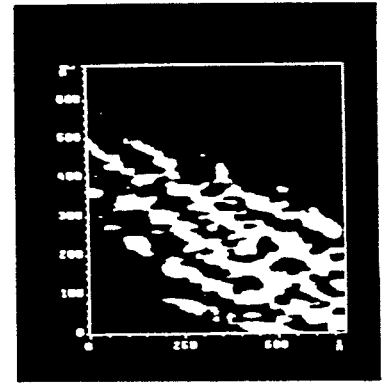
FIG. 3 is a head-on view of a 500 Å by 500 Å region showing several 4-hydroxymercuribenzoate-complexed poly-4-thiouridylic acid molecules crossing the substrate.
Figure 4:
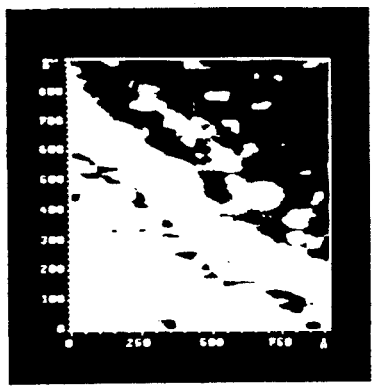
FIG. 4 is a head-on view of a region of about 800 Å by 800 Å covered with an equal mixture of unstained poly (rU), and 4-hydroxymercuribenzoate-complexed poly-4-thiouridylic acid molecules, the top right area being unstained and the lower left being stained fragments.

FIG. 2 shows a 700 Å by 700 Å region of deposits from solution I. FIG. 3 shows a similar view of deposits in a 500 Å by 500 Å region from solution II. While the absolute black to white scale is somewhat arbitrary (as illustrated by the differences in the two molecules imaged in FIG. 1), the degree of modulation in the immediate vicinity of the polymer, in relation to the background height, shows striking changes. This is because the highest parts of the image (with mercury stain) are many times the change from background to the dip as the tip approaches the molecule. This is not the case in the unstained polymer. Of course, in order for this comparison to be made, isolated molecules must be imaged so that the substrate may be used as a reference. In images of packed aggregates, it is hard to distinguish those pictures taken with solution I from those taken with solution II. The relative changes are demonstrated most vividly when the solutions are mixed (solution III). Here one sees a bimodal distribution of contrasts that is not observed when pure samples are imaged. An example is given in FIG. 4. The upper right part of the image is littered with 'low contrast' fragments (presumably poly (rU)) while the lower left is littered with high contrast fragments (presumably poly s$^4$U). In general, the two do not phase separate in this way: most images show a rather confusing mix of 'bright' molecules and 'dark' molecules. In the case of heterogeneous staining of the individual molecules (so the contrast changes along a given molecule), imaging in an aggregate may be advantageous. The molecules are usually held down better in an aggregate, and fluctuations in shape due to sequence are suppressed somewhat.

Figure 5:
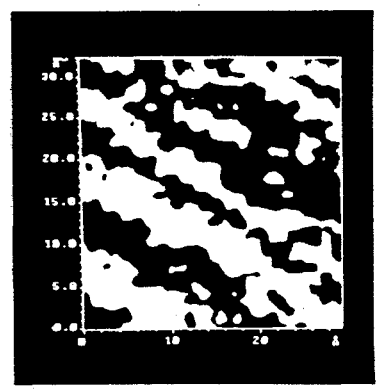
FIG. 5 is a head-on view of a 32 Å × 32 Å region crossed by several RNA strands in which the internucleotide thiophosphate groups adjacent to adenosine nucleosides in specifically thiolated RNA are selectively labeled with 4-hydroxymercuribenzoate. In one strand (close to the center), each nucleotide is clearly visible. The bright spots correspond to the labeled internucleotide phosphate groups adjacent to the $S^1$-sulfur atom of the adenosine nucleotides in the chain.

Such a heterogeneous staining is illustrated in FIG. 5 where several RNA polymers (which have been heterogeneously stained) are shown. In the case of the chain near the center of the image, the resolution is good enough to show each stained base clearly, allowing the location of adenine residues to be read from the image directly. About twenty (20) of the bases are visible in this image.

In a preferred practice of the present invention, the DNA and RNA sample is dissolved to a concentration of 2 micrograms per milliliter in a 5 mM solution of tris-(hydroxymethyl) aminomethane. in D.I. water. A 2.4 mM solution of sodium-p-hydroxymercuribenzoate is added in the amount of 2 microliters per microgram of DNA or RNA.

The resulting RNA solution is inserted into the STM cell and deposited onto the gold substrate by holding the gold substrate at 1 volt positive with respect to a silver/silver chloride reference electrodes for one minute. The substrate is then scanned with the pre-prepared STM tip to form images such as that illustrated in FIGS. 1-5.

The DNA solution is handled in a slightly different way because it must first be denatured. Thus, the DNA solution is placed in a capillary tube adjacent the STM cell and heated to 98° C. for ten minutes to denature the DNA. The resulting heated solution of denatured single stranded DNA is then injected into the STM cell and deposited on the gold substrate by holding it at 1 volt positive with respect to an Ag/AgCl reference electrode for one minute. The substrate is then scanned with the STM tip to form images similar to those shown for RNA.

The invention herein described is believed to be the first practical method ever devised for sequencing nucleic acids by visualization of the bases. Since the operation and data acquisition systems of the STM are usually under digital computer control, the entire process may be automated. The operator would guide the computer in locating target molecules and tracking their path. However, from that point on, the computer could trace the brightness contours along the backbones until the statistics were adequate for sequencing. Thus one machine could image at least 1000 base pairs a minute, a rate that would make the sequencing of the human, genome a finite task (a few man years). A suitable computer-controlled system designed especially for scanning tunneling microscopy which acquires and displays the signal from the moving probe is commercially available from Angstrom Technology, Inc., Mesa, Ariz. (the TAK 2.0 Scanning Tunneling Microscope System).

To further illustrate the present invention and not by way of limitation, the following examples are presented.

EXAMPLE 1

The sequencing method of the present invention is conducted using Lambda bacteriophage DNA as a sequencing target. A portion of this DNA is amplified using the polymerase chain reaction. In the reaction, two primers are used, and the sequences bounded by these primers are determined. As an example, the primer GAT GAG TTC GTG TCC GTA CAA CTG G, together with the primer GGT TAT CGA AAT CAG CCA CAG CGC C, bounds a 500 base-pair target of the Lambda bacteriophage genome. This segment is amplified under the following conditions:

pH 8.3 10 mM tris-HCl, 50 mM KCL, 1.5 mM MgCl2, 0.01% gelatin, 0.2 mM each of dATP, dTTP, dCTP, dGTP, 0.2 micromolar concentration of each primer, 0.2 nanogram of template (Lambda DNA) per 100 microliters final solution, and 2.5 units of TAQ polymerase per 100 microliters.

In each reaction one of the 2'-deoxynucleoside 5'-triphosphates is replaced with the analogous alpha-thio 2'-deoxynucleoside 5'-triphposphate. For example, dTTP is replaced in one reaction with alpha-thio dTTP. Five separate reactions are done, one with each alpha-thionucleoside 5'-triphosphate and one reaction with no alpha-thionucleoside 5'-triphosphate. The reactions with nucleoside 5'-O-(1-thiotriphosphates) are done using following temperature protocol:

Initial melting at 94° C. for one minute, repetitive cycles of 1 minute at 94° C., then 1 minute at 37° C., and then seven minutes at 72° C. is repeated 25 times. At the end of 25 cycles, 2.5 more units of TAQ polymerase are added per 100 microliter reaction volume, and the cycles are resumed 50 more times.

Reactions with no sulfur-containing nucleotides are done in the same way, but the 72 degree step is done for 3 minutes, and the reaction is stopped after 25 cycles. No extra TAQ polymerase is added.

The resulting DNA preparations are then phenol-extracted to remove protein, purified on a membrane filter to remove unreacted primers and mononucleotides, and then sequenced by dissolving the DNA to a concentration of 2 μg/mL in 3 mM solution of tris (hydroxymethyl)aminomethane in distilled water. A 2.4 mM of sodium-4-hydroxy-mercuribezoate is then added in the amount of 2 microliters per each microgram of the DNA.

The DNA solution is then placed in a capillary tube adjacent to the STM cell and heated to 98° C. for ten minutes to denature the DNA. The heated solution is then injected into the STM cell and deposited on the gold substrate by holding it at 1 volt positive with respect to a Ag/AgCl reference electrode for one minute. The substrate is then scanned with the STM tip and the data accumulated.

Any filter that retains the DNA preparation but allows the unreacted starting materials to pass through can be used in the practice of the present invention so long as it does not bind nucleotides irreversibly. Typically, such a filter retains compounds with a molecular mass greater than 100,000 Daltons. A CENTRICON 100 filter is quite suitable for use herein.

EXAMPLE 2

Use of TAQ polymerase to amplify a pSP72 Multiple Cloning DNA Sequence in the presence of Sulfur-Containing Nucleoside Triphosphates, Followed by STM DNA Sequence Determination.

A second example of the sequencing method involves the use of pSP72 Vector DNA as a sequencing target. A portion of this DNA is amplified using the polymerase chain reaction. In this reaction, two primers are used, and the sequences bounded by these primers are determined. As an example, the primer ATTTA GGTGA CACTA TA, together with the primer TAATA CGAC TCAC TATA, bounds a 101 base-pair target of the pSP72 Vector sequence. This segment is amplified under the following conditions:

pH 8.3 10 mM tris-HCl, 50 mM KCl, 1.5 mM MgCl2, 0.01% gelatin, 0.2 mM each of dATP, dTTP, dCTP, 0.2 micromolar concentration of each primer, 0.2 nanogram of template (pSP72 DNA) per 100 microliters final solution, and 2.5 units of TAQ polymerase per 100 microliters.

In each reaction, one of the 2'-deoxynucleoside 5'-triphosphates is replaced with the analogous 2'-deoxynucleoside 5'-triphosphate. For example, dTTP is replaced in one reaction with alpha-thio-dTTP. Five separate reactions are done, one with each alpha thionucleoside 5'-triphosphate and one reaction with no alpha-thionucleoside 5'-triphosphate. The reactions with alpha-thionucleoside 5'triphosphates are done using the following temperature protocol:

Initial melting at 94° C. for one minute, repetitive cycles of 1 minute at 94° C., then 1 minute at 37° C., and then seven minutes at 72° C. is repeated 25 times. At the end of 25 cycles, 2.5 more units of TAQ polymerase are added per 100 microliter reaction volume, and the cycles are resumed 25 more times.

Reactions with no sulfur-containing nucleotides are done in the same way, but the 72° C. step is done for 3 minutes, and the reaction stopped after 25 cycles. No extra TAQ polymerase is added.

The resulting DNA preparations are phenol-extracted to remove protein, purified on a Centricon 100 filter to remove unreacted primers and mononucleotides, and then sequenced using the procedure described in Example 1.

EXAMPLE 3

Use of Reverse Transcriptase to Generate a cDNA Template that is Amplified by TAQ Polymerase in a Polymerase Chain Reaction in the presence of Sulfur-Containing Nucleoside Triphosphates, followed by STM DNA Sequence Determination.

In this sequencing method, rabbit alpha-Globin messenger RNA is used as a sequencing target. This RNA is reverse-transcribed into DNA using reverse transcriptase, and the single-stranded DNA amplified using the polymerase chain reaction. In this reaction, two primers are used, and the sequences bounded by these primers are determined.

The oligodeoxynucleotide d(pT) 12-18 is used in the reverse transcriptase reaction to produce single-stranded cDNA. This cDNA is subjected to PCR amplification using d(pT) 12-18 as one primer and ACACTTCTGGTCCAGTCCGACTGAGA as the other primer, which together bound the following target alpha-globin sequence:

5' end
acacttctggtccagtccgactagagaaggaaccaccatggtgctgtctcccgct
gacaagaccaacatcaagactgcctgggaaaagatcggcagccacggtggcagag
tatggcgccgaggccgtggagaggatgttcttgggcttccccaccaccaagacc
tacttcccccacttcgacttcacccacggctctgagcagatcaaagcccacggc
aagaaggtgtccgaagccctgaccaaggccgtgggccacctggacgacctgccc
ggcgccctgtctactctcagcgacctgcacgcgcacaagctgcgggtggacccg
gtgaatttcaagctcctgtcccactgcctgctggtgaccctggccaaccaccac
cccagtgaattcaccctgcggtgcatgcctccctggacaagttcctggccaac
gtgagcaccgtgctgacctccaaatatcgttaagctggagcctgggagccggcc
tgccctccgccccccccatccccgcagcccaccccctggtctttgaataaagtct
gagtgagtggca - 3' end In the above sequence, "a" indicates an adeylate residue, "c" a cytidylate residue, "g" a guanylate residue, and "t", a thymidylate residue.

One microgram of mRNA, 200 units of Maloney Murine Leukemia Virus reverse transcriptase, 0.3 micrograms of d(pT) 12-18 in pH 8.3 50 mM tris-HCl, 75 mM KCl, 3 mM MgCl₂, 10 units of Human Placental RNAse inhibitor, 3 micrograms of bovine serum albumin, 10 nanomolar concentrations of each of dATP, dTTp, dCTP, dGTP, and 10 mM dithiothreitol are incubated in 30 microliters for one hour at 37° C. Five microliters of the resulting cDNA preparation are subjected to PCR amplification using the following protocol:

A reaction mixture is made that contains at pH 8.3, the following constituents: 10 mM tris-HCl, 50 mM KCl, 1.5 mM MgCl₂, 0.01% gelatin, 0.2 mM each of dATP, dTTP, dCTP, dGTP, 0.2 micromolar concentration of each primer, 5 microliters of cDNA solution per 100 microliters final solution, and 2.5 units of TAQ polymerase per 100 microliters.

In each reaction, one of the 2'-deoxynucleoside 5'-triphosphate is replaced with the analogous alpha-thio-2'-deoxynucleoside 5'-triphosphate. For example, dTTP is replaced in one reaction with alpha-thio-dTTP. Five separate reactions are completed, one with each alpha-thio-nucleoside 5'-triphosphate and one reaction with non alpha-thio-nucleoside 5'-triphospahte. The reaction with the thionucleoside triphosphates are conducted using the following temperature protocol:

Initial melting at 94° C. for one minute. A repetitive cycle of 1 minute at 94° C., then 1 minute at 37° C., and lastly seven minutes at 72° C. is repeated 25 times. At the end of the 25 cycle repetitions, 2.5 more units of TAQ polymerase are added per 100 microliter reaction volume, and the cycle is repeated another 25 times.

Reactions with no sulfur-containing nucleotides are done essentially in the same way, except that the 72° C. step is done for 3 minutes, and the reaction is stopped after 25 cycles. No extra TAQ polymerase is added.

The resulting DNA preparations are phenol-extracted to remove protein, purified on a Centricon 100 filter to remove unreacted primers and mononucleotides, and then sequenced using the procedure of Example 1.

EXAMPLE 4

Use of Reverse Transcriptase to Generate cDNA Primer in the presence of Sulfur-Containing Nucleoside Triphosphates, followed by STM DNA Sequence Determination.

The sequencing method is repeated using rabbit beta-Globin messenger RNA as a sequencing target in the absence of PCR amplification of cDNA. In this case, mRNA is reverse-transcribed into DNA using reverse transcriptase in the presence of sulfur-containing 2'-deoxynucleoside 5'-triphosphates.

For example, an oligodeoxynucleotide d(pT) 12-18 is used in the reverse transcriptase reaction to produce sulfur-substituted single-stranded cDNA. This is realized using the following conditions.

One microgram of mRNA, 200 units of Maloney Murine Leukemia Virus reverse transcriptase, 0.3 micrograms of d(pT) 12-18 in 50 mM tris-HCl, pH 8.3 buffer containing 75 mM KCl, 3 mM MgCl₂, 10 units of human placental RNAse inhibitor, 3 micrograms of bovine serum albumin, 10 nanomolar concentrations of each dATP, dTTP, dCTP, dGTP, and 10 mM dithiothreitol are incubated in 30 microliters for one hour at 37° C.

In each reaction, one of the 2'-deoxynucleoside triphosphates is replaced with the analogous alpha-thio 2'-deoxynucleoside 5'-triphosphate. For example, dTTP is replaced in one reaction with alpha-thio-dTTP. Five separate reactions are done, one with each alpha-thio-nucleoside 5'-triphosphate and one reaction with no alpha thionucleoside 5-triphosphate.

The resulting DNA preparations are phenol-extracted to remove protein, purified on a membrane filter (as shown in Example 1) to remove unreacted primers and mononucleotides, and then sequenced in the manner described in Example 1.

EXAMPLE 5

Use of RNA Polymerase to Generate RNA Transcripts in the presence of Sulfur containing Ribonucleoside Triphosphates, followed by STM RNA Sequence Determination.

Linearized plasmid DNA containing an SP6 promoter region is constructed using the state of the art (See: Melton et al, *Nucleic Acid Research*, vol. 12, pp. 7035-56 (1984).) An example of such a plasmid DNA is the pSP64 Vector. This contains the (ATTTA GGTCA CACTA TA) SP6 Promoter sequence. RNA generated by the interaction of this vector and SP6 RNA polymerase is sequenced by the following procedure:

Five-fold concentrated translation buffer is made containing: 200 mM tris-HCl pH 7.5, 30 mM $MgCl_2$, 10 mM Spermidine, and 50 mM NaCl.

20 microliters of the concentrated transcription buffer are added to 10 microliters of 100 mM dithiothreitol, 4 microliters of 25 units/ml human placental ribonuclease inhibitor, and 20 microliters of a solution that contains 12.5 mM for each of ATP, GTP, CTP, and UTP. 2 microliters (four micrograms) of linearized plasmid DNA and 50 units of SP6 RNA Polymerase are added. The final volume is increased to 100 microliters with autoclaved water. This mixture is incubated for two hours at 37° C.

In each, reaction, one of the ribonucleoside 5'-triphosphates is replaced with the analogous alpha-thioribonucleoside 5'-triphosphate. For example, the UTP is replaced in one reaction with alpha thio-UTP. Five separate reactions are done, one with each alpha-thionucleoside 5'-triphosphate and one reaction with no alpha thionucleoside 5'-triphosphate. After completion of the reaction, template DNA is removed by adding four units of bovine pancreas DNAse. The solutions are incubated for fifteen minutes at 37° C.

The resulting RNA preparations are phenol-extracted to remove protein, chloroform-extracted to remove phenol, and purified on a Centricon 100 filter to remove mononucleotides. The result RNA solution is then inserted into the STM cell and deposited onto the gold substrate by holding the gold substrate at 1 volt positive with respect to a Ag/Ag Cl reference electrode for one minute. The substrate was then scanned with the STM tip to determine the sequence of the RNA.

EXAMPLE 6

Use of Nick Translation with DNA Polymerase and Sulfur-containing 2'-deoxyribonucleoside 5'-triphosphates to sequence DNA by the STM method.

In this example, nicked dsDNA is reacted with *E. Coli* DNA Polymerase I in the absence of an exogenous primer.

Ten-fold concentrated nick translation buffer consists of 500 mM tris-HCl, pH 7.2, 10 mM magnesium sulfate, and 1 mM dithiothreitol.

Five microliters of the nick translation buffer, five microliters (0.2 micrograms./ml) of target DNA (in this case Lambda phage DNA), five microliters containing one unit/microliter DNA polymerase and 0.2 ng/microliter pancreatic DNAse, ten microliters of a solution containing three normal 2'-deoxyribonucleoside 5'-triphosphates, each at a concentration of 0.2 mM, five microliters of a 0.4 mM solution of the sulfur-containing 2'-deoxyribonucleoside 5'-triphosphate, and sufficient water for a final volume of fifty microliters are reacted for one hour at 15° C. Five microliters of 0.25 M EDTA are then added to stop the reaction.

The resulting DNA preparation is phenol-extracted to remove protein, chloroform -extracted to remove phenol, and purified on a membrane filter (as shown in Examples) to remove mononucleotides and primers. The DNA solution is then sequenced using the procedure of Example 1.

From the foregoing, it becomes apparent that new and useful procedures have been herein described and illustrated which fulfill all of the aforestated objectives in a remarkably unexpected fashion. It is of course understood that such modifications, alterations, adaptations and chemical substitutions as may readily occur to an artisan having the ordinary skills to which this invention pertains are intended within the spirit of the present invention which is limited only by the scope of the claims appended hereto.

Accordingly, what is claimed is:

1. A method for the determination of the nucleotide sequence of DNA and RNA with a scanning probe microscope having a tip, said method comprising:
  (a) contacting a DNA or RNA sample with a polymerase in the presence of a sulfur-containing nucleoside 5'-triphosphate to form an amplified DNA or RNA polymer containing a sulfur-containing nucleotide;
  (b) contacting said amplified polymer with a nonchelated soluble organometallic compound to form a metal-complexed nucleic acid polymer;
  (c) disposing said metal-complexed nucleic acid polymer on a substrate which is flat to within a few atoms across an area of several square microns;
  (d) passing said tip of said scanning microscope in a probe path over the surface of said polymer to measure electrical conductivity or potential therebetween; and
  (e) recording the difference in electrical conductivity or potential so measured at preselected increments along said scanning probe path to identify the location of nucleoside bases to determine the sequence of said DNA nucleoside bases.

2. A method according to claim 1 in which said soluble organometallic compound contains a metal selected from the group consisting of mercury, silver, bismuth, cadmium, cerium, cobalt, copper, iron, lanthanum, manganese, nickel, lead, platinum, tin, titanium and zinc.

3. A method according to claim 1 in which said microscope is a scanning-tunnel microscope.

4. A method according to claim 1 in which said microscope is atomic-force microscope.

5. A method for visualizing the base sequence of nucleic acid polymers with a scanning probe microscope having a tip, said method comprising forming a sulfur-containing polynucleotide; placing said sulfur-containing polynucleotide into a solution containing a soluble mercury compound to complex said mercury-containing compound with the sulfur-containing polynucleotide; depositing said mercury-complexed nucleic acid polymer on a gold substrate which is flat to within a few atoms over an area of several square microns; passing the tip of said scanning microscope in a path over the surface of said deposited polymer to measure conductivity or potential therebetween; and recording the difference in electrical conductivity or electrical potential so measured at preselected increments along said scanning probe path.

6. A method according to claim 5 in which said nucleic acid polymer is selected from the group consisting of DNA and RNA.

7. A method according to claim 6 in which said microscope is a scanning-tunnel microscope.

8. A method according to claim 6 in which said microscope is atomic-force microscope.

9. A method according to claim 5 in which said substrate is prepared by depositing Angstrom amounts of gold epitaxially on freshly cleaned scratch-free mica in an ultra high vacuum system.

10. A method according to claim 9 in which said gold-bearing mica is preheated to about 300° C. in a oil-free system at least $10^{-9}$ torr, removed from said system, and stored under argon until needed.

11. A method according to claim 5 in which said tip is formed of Pt-Ir wire.

12. A method according to claim 11 in which said tip is pretreated by immersing said tip into a solution of 3M NaCN and 1M NaOH, applying 20 volts of a c to said immersed tip until 0.5 Amperes rms. flows therethrough; stopping the current flow; applying small bursts of current to said tip until the lower region thereof parts; pressing said tip through a film of hard wax preheated to a temperature of from 100° C. to about 200° C. to deposit wax on said tip; and removing said wax-coated tip from said wax.

13. A method for visualizing the base sequence of a nucleic acid polymer selected from the group consisting of DNA and RNA with a scanning tunneling microscope having a tip operatively associated therewith, said method comprising placing said nucleic acid polymer into a solution containing a compound having a sulfur atom capable of replacing the oxygen atom in said polymer; dissolving said oxygen-reduced polymer in a buffer solution; depositing said polymer-containing buffer solution in a cell having a gold substrate; introducing sodium 4-hydroxymercuribenzoate into said cell; inserting a Pt-Ir wire counter electrode into said cell under a 2 V bias to cause hydrogen to evolve therefrom; lowering said tip toward said substrate to measure the difference in electrical conductivity at preselected increments thereof along a predefined path; and translating said differences in electrical conductivity or electrical potential into a visual pattern representing the base sequence of said nucleic acid polymer.

14. A method according to claim 13 in which said compound is a thiophosphate.

15. A method according to claim 14 in which said thiophosphate is alpha 2'-thio-deoxynucleoside 5'-triphosphate.

16. A method for visualizing the base sequence of nucleic acid polymers with a scanning probe microscope having a tip, the method comprising: forming a sulfur-containing polynucleotide; placing said sulfur-containing polynucleotide into a solution containing a soluble cation-containing compound, said cation being selected from the group consisting of mercury, silver, bismuth, cadmium, cerium, cobalt, copper, iron, lanthanum, manganese, nickel, lead, platinum, tin, titanium and zinc, to complex said cation-containing compound with said sulfur-containing polynucleotide; depositing said cation-complexed nucleic acid polymer on a gold substrate flat to within a few atoms; passing the tip of said scanning microscope in a path over the surface of said polymer to measure electrical conductivity or electrical potential therebetween; and recording the difference in electrical conductivity or electrical potential so measured at preselected increments along said scanning probe path.

17. A method according to claim 14 in which said cation is mercury.

18. A method according to claim 17 in which said mercury is contained in a soluble mercury salt.

19. A method according to claim 17 in which said mercury is contained in a soluble alkyl mercury compound.

20. A method according to claim 17 in which said mercury is contained in a soluble aryl mercury compound.

* * * * *